United States Patent [19]

Miyagi

[11] Patent Number: 4,878,484
[45] Date of Patent: Nov. 7, 1989

[54] WATER-TIGHT ENDOSCOPE

[75] Inventor: Kunihiko Miyagi, Tokyo, Japan

[73] Assignee: Machida Endoscope Co., Ltd., Tokyo, Japan

[21] Appl. No.: 219,251

[22] Filed: Jul. 15, 1988

[51] Int. Cl.⁴ .............................................. A61B 1/00
[52] U.S. Cl. ....................................................... 128/4
[58] Field of Search ..................... 128/4, 5, 6, 7, 8, 3, 128/DIG. 14

[56] References Cited

U.S. PATENT DOCUMENTS 4,545,369 10/1985 Sato ........................................ 128/4

OTHER PUBLICATIONS

Expanded PTFE: It's a Whole New Ball Game, Reprinted from the Jul. 1971 Issue of Plastics World, W. L. Gore & Assoc.

Primary Examiner—William H. Grieb
Attorney, Agent, or Firm—Peter L. Berger

[57] ABSTRACT

A water-tight endoscope comprising a flexible tube zone, a handle zone and a guide tube zone is disclosed. Each of the flexible tube zone, the handle zone and the guide tube zone has a water-tight structure, and moreover, a connecting part for each zone has a water-tight structure. An opening for connecting the interior of the endoscope to the outer air is formed in the guide tube zone and a waterproof and breathable filter is arranged in this opening. By this arrangement, the interior of the endoscope is connected to the outer air through the waterproof and breathable filter.

5 Claims, 3 Drawing Sheets

WATER-TIGHT ENDOSCOPE

BACKGROUND OF THE INVENTION

The present invention relates to a water-tight endoscope comprising a flexible tube zone, a handle zone and a guide tube zone.

At the present, an endoscope which has been used for observation and clinical treatment in the colon is washed and disinfected and is then used again.

Accordingly, such an endoscope has an entirely water-tight structure so that at the washing step, washing water is not allowed to intrude into the interior of the endoscope.

In this water-tight endoscope comprising as constituent elements a flexible tube, a handle and a guide tube, these elements and connecting parts of these elements are completely sealed and the interior of the endoscope is sealed from the outer air.

In general, disinfection of an endoscope is carried out in an atmosphere of ethylene oxide gas (hereinafter referred to as "EOG") maintained at about 55° C.

In the conventional water-tight endoscope having the above-mentioned structure, however, since the respective elements and the connecting parts thereof are completely sealed, the structure is not only water-tight but also airtight.

Therefore, if the conventional water-tight endoscope having the above mentioned structure is warmed to about 55° C. at the disinfection treatment, the soft outer sheath of the flexible tube, especially an angle part, is swollen like a balloon.

Accordingly, swelling is repeated at every disinfection, resulting in the elastic fatigue, and a problem of reduction of the durability of the flexible tube is brought about by this elastic fatigue.

In the case where this swelling is extreme, the flexible tube bursts, and large-scaled repairing becomes necessary.

SUMMARY OF THE INVENTION

In accordance with the present invention, there is provided a water-tight endoscope in which the interior of the endoscope is connected to the outer air through a waterproof and breathable filter. This novel endoscope has a water-tight structure but this water-tight structure is not air tight.

More specifically, in accordance with the present invention, there is provided a water-tight endoscope comprising a flexible tube zone, a handle zone and a guide tube zone, the respective zones and connecting parts thereof having a water-tight structure, wherein an opening for connecting the interior of the endoscope to the outer air is formed in the guide tube zone and a waterproof and breathable filter is arranged in the opening to connect the interior of the endoscope to the outer air.

It is a primary object of the present invention to provide an endoscope in which air in the interior of the endoscope, which is swollen at the disinfection step, is caused to escape to the outside, and the burden on the respective members of the endoscope by swelling of air is eliminated.

Another object of the present invention is to provide a water-tight endoscope having a reliable water-tight structure.

Still another object of the present invention is to provide a durable water-tight endoscope in which the burden on the respective members by swelling of air in the interior of the endoscope is eliminated.

DETAILED DESCRIPTION OF THE PREFERRED EMBODIMENTS

The first embodiment of the present invention will now be described with reference to FIGS. 1 through 3.

Figure 1:
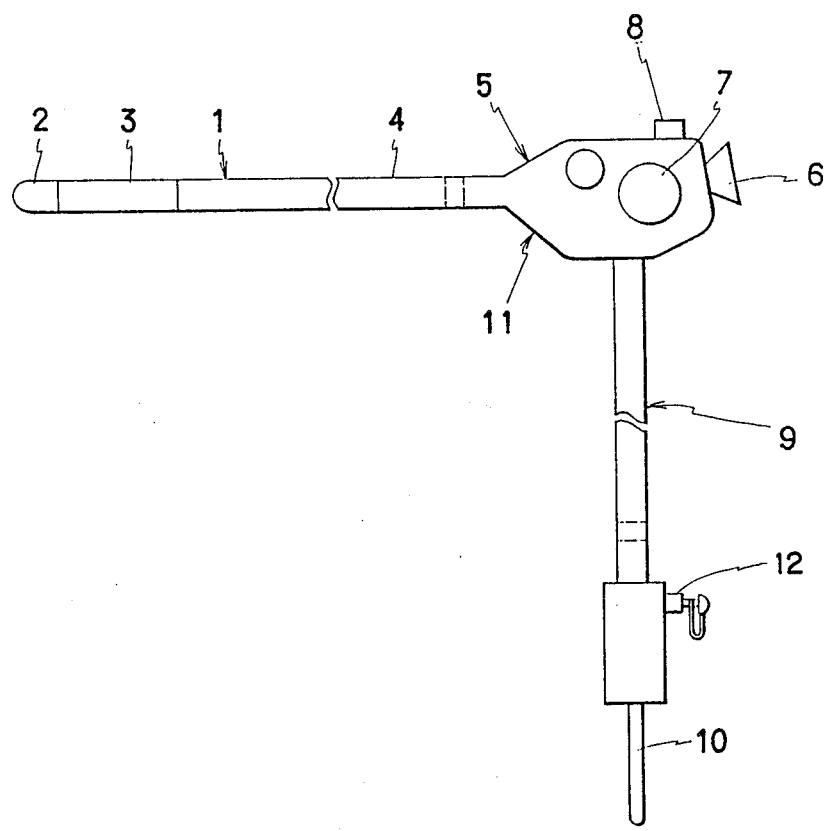
FIG. 1 is a side view showing the first embodiment of the present invention.

Referring to FIG. 1, a flexible tube zone 1 comprises a rigid part 2 including an observing window on the the end an, illuminating window, a forceps opening and an opening for jetting air and water, an angle part 3 for changing the observation direction of the observing window and an adjacent flexible tube 4.

In general, an image guide, an optical guide, an air and water feed pipe, a suction pipe, a forceps guide pipe, an angle-operating wire and the like are laid out in the flexible tube zone 1.

A handle zone 5 includes an eyepiece part 6, an angle-operating dial 7 and a forceps introduction opening 8.

A guide tube zone 9 is disposed to guide the above-mentioned optical guide and water and air feed pipe collectively as one or dividedlyd in the plural. In the present embodiment, they are guided collectively as one. A connecting plug 10 is disposed to connect the endoscope to a light source device (not shown) or the like.

Each of the connecting parts of the flexible tube zone 1, the handle zone 5 and the guide tube zone 9 has a water-tight, air-tight structure and an endoscope 11 is thus constructed as a whole.

Figure 2:
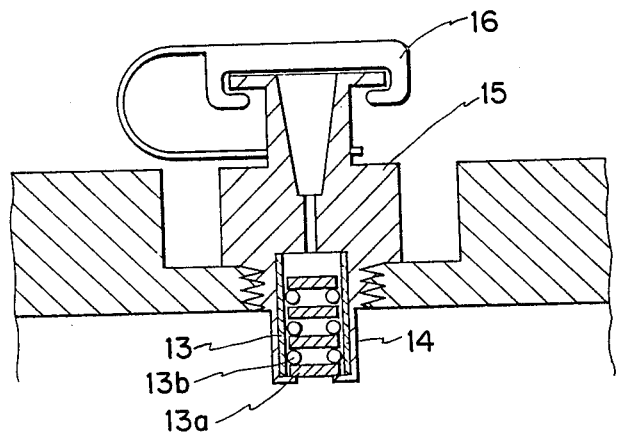
FIG. 2 is a sectional side view illustrating the main part of the first embodiment shown in FIG. 1 in the state where a plug is closed.
Figure 3:
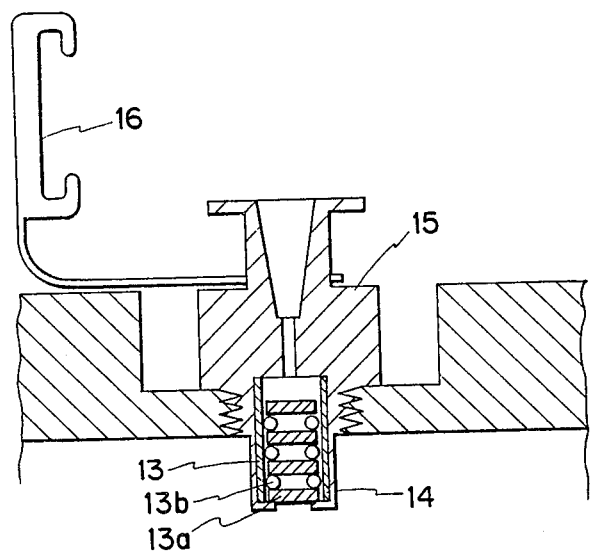
FIG. 3 is a sectional side view illustrating the main part of the first embodiment shown in FIG. 1 in the state where the plug is opened.

Referring to FIG. 2, a plug 12 is attached to the guide tube zone 9 to connect the interior of the endoscope 11 to the outer air. This structure will now be described in detail.

A filter cylinder 13 is attached to an opening 14 formed in the guide tube zone 9, and one side of the filter cylinder 13 is opened to the interior of the guide tube zone 9 and the other side is opened to the outer air. The filter cylinder 13 is attached to the opening 14 by such means as screws. A filter 13a composed of a waterproof and breathable material, for example, GORE-TEX (registered trademark), polytetrafluoroethylene porous mold, etc., is placed in the interior of the filter cylinder 13. Incidentally, in the present embodiment, a plurality of filters 13a are arranged with spacers 13b being interposed between every two adjacent filters 13a.

A plug 15 is attached to the guide tube zone 9 and connected to the filter cylinder 13, and the plug 15 has a cap 16.

In the above-mentioned structure, the cap 16 is fitted on the plug 15 in the normal state and the endoscope is used for such an operation as observation in this state. Dust or the like is not allowed to intrude into the interior of the plug 15 because the plug 15 is closed by the cap 16.

After the observation, the endoscope is washed and disinfected, and washing is carried out in the state where the cap 16 is attached to the plug 15.

At the disinfection step, the cap 16 is taken out and the plug 15 is placed in the open state, and the interior of the endoscope is connected to the outer air. This connection is established through the filter cylinder 13, and therefore, air in the endoscope is allowed to flow but water and moisture are shut from the interior of the endoscope. In this state, disinfection is carried out with EOG at an elevated temperature. The pressure in the flexible tube zone of the endoscope becomes equal to the pressure of the outer air, and disinfection can be conducted without swelling of air by elevation of the temperature.

After completion of the disinfection, the cap 16 is fitted on the plug 15 to restore the original state.

If clogging is caused in the filter 13a, the filter cylinder 13 is exchanged with fresh one.

In the above-mentioned sturucture, disposition of the plug and cap is not absolutely necessary, and a structure in which only the filter cylinder is attached to the opening 14 is sufficient. In this case, in order to prevent adhesion of dust or the like, it is preferred that the outer air side of the filter cylinder be on the same plane as the circumferential face of the guide tube zone or slightly projected therefrom. In this case, the endoscope is always kept in the open state.

Of course, a closed state may be produced by attaching a cap to the filter cylinder according to need.

Figure 4:
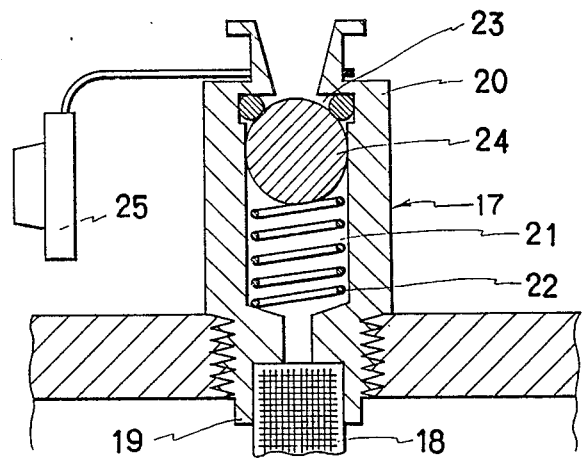
FIG. 4 is a sectional side view illustrating the main part of the second embodiment of the present invention in the state where a valve is closed.
Figure 5:
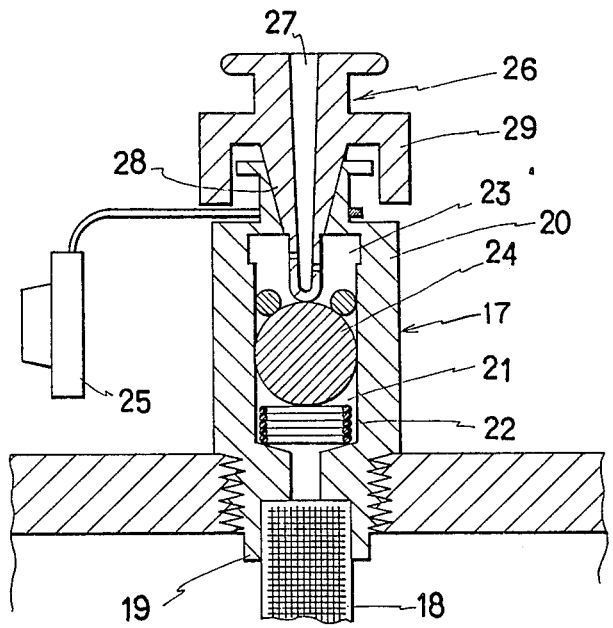
FIG. 5 is a sectional side view illustrating the main part of the second embodiment in the state where the valve is opened.

The second embodiment of the present invention will now be described with reference to FIGS. 4 and 5.

A valve 17 is attached to the guide tube zone 9 so that the interior of the endoscope 11 is connected to the outer air through this valve 17. This structure will now be described in detail.

A filter cylinder 18 is attached to an opening 19 formed in the guide tube zone 9, and one side of the filter cylinder 18 is opened to the interior of the guide tube zone 9 and the other side is opened to the outer air. The filter cylinder 18 is attached to the opening 19 by such means as screws. A filter composed of waterproof and breathable material, for example, GORETEX (registered trademark), polytetrafluoroethylene porous mold, etc., is contained in the interior of the filter cylinder 18.

Reference numeral 20 represents a valve body. The type of the valve means 17 is not particularly critical. For example, as show in the drawings, there may be adopted a structure in which a valve 24 is pressed to a valve opening 23 by a spring 22 in a valve chamber 21, and the top end of the valve body 20 is connected to the filter cylinder 18. Incidentally, reference numeral 25 represents a cap.

Reference numeral 26 represents a member for opening the valve body 20 and is formed separately from the valve body 20. This opening member 26 has a pressing portion 28 having a connecting hole 27 for connecting the valve chamber to the outer air. Reference numeral 29 represents an anchoring portion.

In the above-mentioned structure, the valve 24 is closed by the pressing force of the spring 22 in the normal state, and in this state the endoscope is used for such an operation as observation. The valve body 20 is closed by the cap 25 to prevent intrusion of dust or the like.

After the observation, the endoscope is washed and disinfected. Washing is carried out in the state where the cap 25 is attached to the valve body 20.

At the disinfection step, the cap 25 is taken out and the opening member 26 is pressed into the valve body 20 and the valve 24 is pressed by the pressing portion 28 against the force of the valve spring 22 to produce the open state. The opening state of the opening member 26 is maintained by the anchoring portion 29 whereby the interior of the endoscope is kept connected to the outer air.

Since this connection state is realized through the filter cylinder 18, air in the endoscope is allowed to flow but intrusion of water and moisture is completely prevented. Disinfection with EOG is carried out in this state. Even if the temperature of EOG is 55° C., the pressure in the flexible tube zone becomes equal to the pressure of the outer air, and disinfection can be conducted without swelling of air by elevation of the temperature.

After completion of the disinfection, the opening member 26 is taken out to restore the original state, and the cap 25 is fitted again.

If a filter is clogged, the filter cylinder 18 can be exchanged with fresh one.

What is claimed is:

1. A water-tight endoscope comprising a flexible tube zone, a handle zone and a guide tube zone, the respective zones and connecting parts thereof having a water-tight structure, wherein an opening for connecting the interior of the endoscope to the outer air is formed in the guide tube zone and a waterproof and gas breathable filter is arranged in said opening to connect gas within the interior of the endoscope to the outer gas, said filter capable of being constantly open for passage of air into and out of the interior of said endoscope during all temperature stages of a disinfecting, temperature-related procedure.

2. A water-tight endoscope as set forth in claim 1, wherein a plurality of waterproof and breathable filters are arranged.

3. A water-tight endoscope as set forth in claim 1, wherein the waterproof and breathable filter is placed in the interior of a filter cylinder and the filter cylinder is fitted in the opening.

4. A water-tight endoscope as claimed in claim 1, wherein a cap is provided to said filter for selectively opening of gas into said interior of said endoscope.

5. A water-tight endoscope comprising a flexible tube zone, a handle zone and a guide tube zone, the respective zones and connecting parts thereof having a water-tight structure, wherein an opening for connecting the interior of the endoscope to the outer air is formed in the guide tube zone, and waterproof and breathable filter and a valve body are arranged in the opening so that only when the valve body is opened, the interior of the endoscope is connected to the outer air.

* * * * *